United States Patent [19]

Buscemi

[11] Patent Number: 5,593,403
[45] Date of Patent: Jan. 14, 1997

[54] METHOD FOR MODIFYING A STENT IN AN IMPLANTED SITE

[75] Inventor: Paul J. Buscemi, Long Lake, Minn.

[73] Assignee: SciMed Life Systems Inc., Maple Grove, Minn.

[21] Appl. No.: 306,008

[22] Filed: Sep. 14, 1994

[51] Int. Cl.⁶ .......................... A61B 17/00; A61B 17/04; A61F 2/04
[52] U.S. Cl. .................................................. 606/2; 606/15
[58] Field of Search ...................... 606/152, 153, 606/154, 155, 8, 15, 16, 13, 14, 27, 128

[56] References Cited

U.S. PATENT DOCUMENTS

| | | |
|---|---|---|
| 1,612,697 | 3/1926 | Cecil . |
| 1,677,671 | 7/1928 | Councill . |
| 3,843,865 | 10/1974 | Nath . |
| 4,207,874 | 6/1980 | Choy . |
| 4,572,186 | 2/1986 | Gould et al. . |
| 4,770,176 | 9/1988 | McGreevy et al. . |
| 4,770,653 | 9/1988 | Shturman . |
| 4,788,975 | 12/1988 | Shturman et al. . |
| 4,848,336 | 7/1980 | Fox et al. . |
| 4,878,492 | 11/1989 | Sinofsky et al. . |
| 4,887,600 | 12/1989 | Watson et al. . |
| 4,920,962 | 5/1990 | Proulx ........................ 606/152 |
| 5,037,427 | 8/1991 | Harada et al. . |
| 5,085,629 | 2/1992 | Goldberg et al. ............ 606/154 |
| 5,098,440 | 3/1992 | Hillstead . |
| 5,109,338 | 4/1992 | Ermert et al. ............... 606/128 |
| 5,364,389 | 11/1994 | Anderson ...................... 606/8 |

OTHER PUBLICATIONS

"Laser Surgery In Enclosed Spaces: A Review", *Lasers in Surgery and Medicine* 5:199–218 (1985), Macruz et al.
"Selective Photothermolysis: Precise Microsurgery by Selective Absorption of Pulsed Radiation", *Science* vol. 220, 27 Jan., 1983.
"Laser Angioplasty: Morphologic Studies, Laser Ablation of Human Atherosclerotic Plaque Without Adjacent Tissue Injury", 1985 by the *American College of Cardiology*, Grundfest et al.
"Absence of Thermal Tissue Injury Using a Pulsed Mode Nq-YAG Laser", Paul H. Gibson et al., Abstracts *Circulation*, vol. 72, Supp III, Oct., 1985.
"Laser-induced Shockwave Lithotripsy of Gallstones", Ch. Ell et al., *Endoscopy* 18, (1986) 95–96.
"Fragmentation of Gallstones by Extracorporeal Shock Waves", Tilman Sauerbruch, M.D., et al., *The New England Journal of Medicine*, Mar. 27, 1986, vol. 314, No. 13.
"Pulsed Ultraviolet Lasers and the Potential for Safe Laser Angioplasty", *The american Journal of Surgery*, vol. 150, Aug. 1985, Grundfest et al.

*Primary Examiner*—Angela D. Sykes
*Assistant Examiner*—Sonya Harris-Ogugua
*Attorney, Agent, or Firm*—Vidas, Arrett & Steinkraus, P.A.

[57] ABSTRACT

A stent in an implanted site is subjected to pulses of laser or sonic energy from external means thereby altering its physical structure without substantially altering or damaging tissue surrounding the implanted site.

11 Claims, 2 Drawing Sheets

METHOD FOR MODIFYING A STENT IN AN IMPLANTED SITE

BACKGROUND OF THE INVENTION

1. Field of the Invention

This invention relates to a method for modifying a stent in an implanted site, and more particularly to a method of altering any stent in an implanted site by subjecting the stent to pulses of laser energy from external means thereby altering their physical structure without substantially altering or damaging tissue surrounding the implanted site.

2. Description of the Related Art

The use of lasers to break down a calculus, stone or calcified tissue for removal from within the human body is disclosed in Watson et al., U.S. Pat. No. 4,887,600. Watson et al. refer to the delivery of a laser beam via an optical fiber to break down these materials for removal from within the human body. A ureterscope with a dye laser is inserted to reach the site of a stone, such that the distal face of a fiber thereof contacts the stone. After irrigation of the site so that the stone is surrounded by liquid, pulses of laser energy at a wavelength between 450 and 550 nm are delivered at not exceeding about 200 millijoules per pulse at a repetition rate of between 10 and 50 Hertz. The stone breaks down into a combination of about 10% vapor, the remainder being easily removed sand-like particles. An excimer laser is noted as being less desirable. An excimer laser will produce a breakdown product of approximately 90% vapor. Watson discloses only breakdown of urinary calculi, gallstones, arterial plaque and calcified tissue.

Artificially induced degradation of stents has not previously been disclosed. A need exists to provide a method of ablating biodegradable stents. Further, a need exists for a method of vaporizing or accelerating the degradation of biodegradable stents through extracorporeal means. A need also exists for a method of altering the physical structure of any implanted stent without substantially altering or damaging the tissue surrounding it.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56 (a) exists.

SUMMARY OF THE INVENTION

The present invention provides a method for modifying a stent made of any material in an implanted site, wherein the stent is subjected to pulses of laser energy from external means. The physical structure of the stent is thereby altered without substantially affecting the tissue surrounding the implanted site.

The present invention also provides a method for effecting the immediate degradation of polymeric stents by delivery of a laser pulse or sonic energy.

Biodegradable polymeric stents reach various states of degradation and pliability as a function of time and position. Such stents tend to become less pliable as degradation proceeds. They may become more pliable immediately upon exposure to water, but generally as the molecular weight of the stent materials becomes lower, they loose their ability to flex and therefore may become considerably more brittle.

Although biodegradable polymeric stents may function well over a short period of time, it may be preferred or advantageous to remove them after weeks or months of implantation due to such factors as loss of flexibility. These devices may be removed by connecting them to a catheter manifold wire of some similar device. Connections, however, would not only cause continuous exposure of the insertion site to the possibility of infection, but would also limit the mobility of the patient.

For the reasons stated above, it would be advantageous if the device could be essentially destroyed in situ. This could be accomplished in several ways. The composition of the polymer may be such that it becomes more brittle with time. In such a situation, blasts of sonic energy could totally disrupt the material into micro particles. Alternatively, the stent material may be made to absorb a dye and subsequently be exposed to light of a specific wavelength that will degrade the stent.

Biodegradable polymeric stents may be pulverized even within tissue by sonic blasts of energy accelerating their dissolution by destroying the physical structure of the biodegradable polymeric stents. This process may be effected internally or by means exterior to the body.

Further, it may not be necessary to remove a device entirely. Once its function is considered to be rendered, it may be appropriate to simply accelerate the degradation process for instance by creating holes or pores in the material to permit greater diffusion of water.

Essentially any polymeric material may be removed by this method. The stent does not necessarily have to be made of a biodegradable material. Materials such as polyethylene terephthalate or PTFE could also be degraded by this method, but would take a greater amount of energy relative to a partially degraded biodegradable or resorbable stent.

The method disclosed herein may also be utilized to degrade or alter metal stents. For example, metal stents could be weakened or modified by breaking or weakening hinge points thereof for example. Entire stents could not as easily be removed, however, because of their mass.

DESCRIPTION OF THE PREFERRED EMBODIMENTS

The present invention provides a method for modifying a stent in an implanted site by subjecting the stent to pulses of laser energy or sonic energy from external means. The physical structure of the stent is thereby altered without substantially affecting the tissue surrounding the implanted site.

The present invention also provides a method for effecting the immediate degradation of stents which have been implanted in a vessel, by delivery of a laser pulse or sonic energy, either internally, or by means external to the body of the organism in which the stent has been implanted.

The method of the present invention may be utilized to alter the physical structure of a stent or essentially destroy a stent in situ.

Where a stent is made of metal, the present method may be utilized to weaken or modify the stent by breaking or weakening hinge points thereof for example. Entire metal stents could not as easily be removed, however, because of their mass.

Where the stent is made of polymeric material, it may not be necessary to remove a device entirely. Once its function is considered to be rendered, it may be appropriate to simply accelerate the degradation process for instance by creating holes or pores in the material to permit greater diffusion of water.

Subjecting a stent made of polymeric material to blasts of sonic energy could totally disrupt the stent material into micro particles. Alternatively, the stent material may be made to absorb a dye and subsequently exposed to light of a specific wavelength. A biodegradable polymeric stent may be pulverized even within tissue by subjecting it to sonic blasts of energy, accelerating its dissolution by destroying its physical structure.

Figure 1:
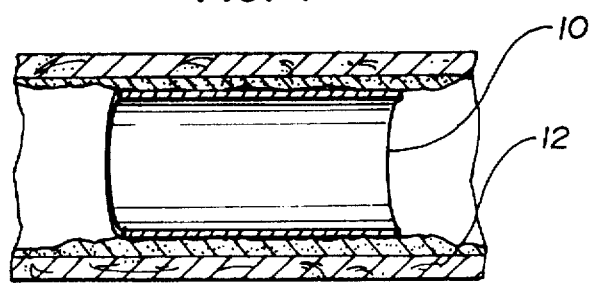
FIG. 1 is a cross sectional view of a vessel with a biodegradable stent in place therein.
Figure 2:
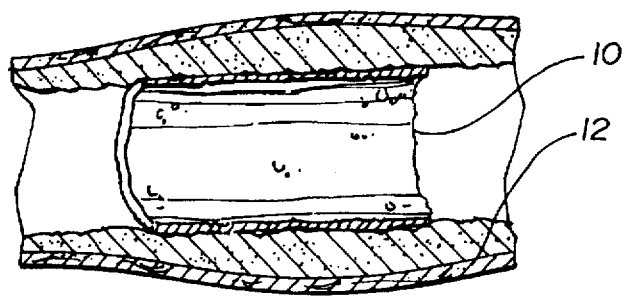
FIG. 2 is a cross sectional view of a vessel in which a biodegradable stent has been in place for a sufficient length of time to be partially absorbed.

Referring to the Figures, at FIG. 1 biodegradable polymeric stent 10 is shown in place implanted in vessel 12. Implanted biodegradable stent 10 which has been in place in vessel 12 for a sufficient length of time to be partially degraded is shown in FIG. 2.

Although laser energy is of known use in the ablation or lithotripsy of urinary calculi, gallstones and arterial plaque, it has been unexpectedly found that laser energy may be applied to vaporize a biodegradable polymeric stent which is in need of removal. Materials that could be modified, altered, or removed include but are not limited to polyactides, polyglycolides, polycaprolactone, polyesters in general, carbohydrates, crosslinked collagen, combinations of polyesters and collagen or polycarbohydrates and collagen, polyethylenes and combinations of polyethylenes and biological materials such as collagen.

Essentially any polymeric material may be removed by this method. The stent does not necessarily have to be made of a biodegradable material. Materials such as polyethylene terephthalate or PTFE could also be degraded by this method, but would take a greater amount of energy relative to a partially degraded biodegradable or resorbable stent.

Figure 3:
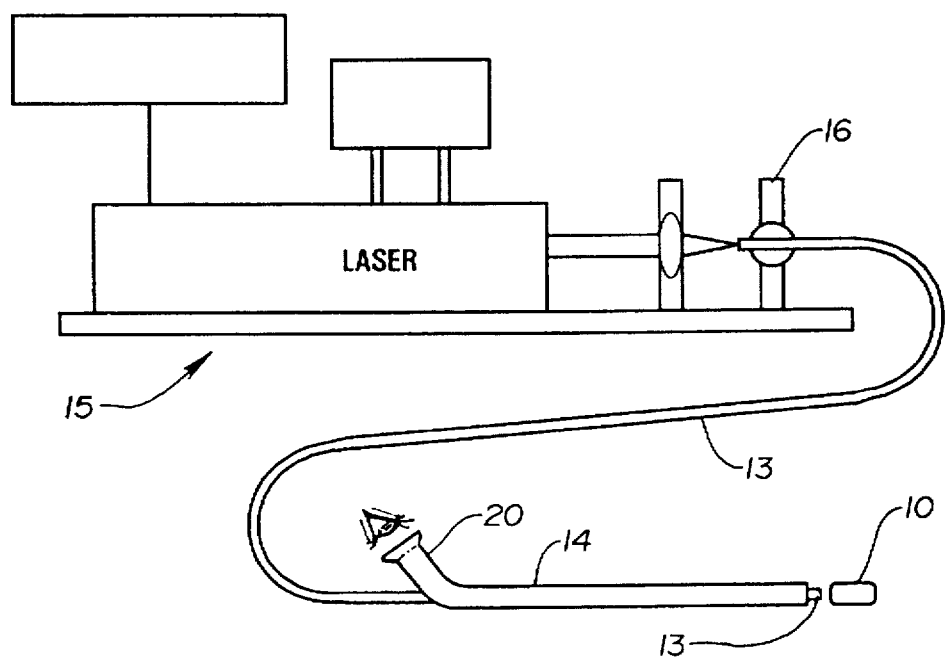
FIG. 3 is a diagram of a system for breaking down a stent via laser.

Referring now to FIG. 3, a diagram of a system for breaking down an unwanted biodegradable polymeric stent through the use of laser energy is shown. Stent 10 is contacted by optical fiber 13, which passes through laser catheter 14 and extends to laser source 15 where proximal end of fiber 13 is held in a fiber mount 16. The most preferred optical fiber would have a diameter less than about 600 microns.

The proximal end of fiber 13 receives a beam from laser source 15. Laser catheter 14 includes an eyepiece 20 through which the user can observe stent 10 and the distal end of fiber 13, in addition to a light source (not shown) to illuminate the distal end of the fiber for viewing and an irrigation lumen to deliver an irrigant to the distal end. Any of a large selection of small diameter optic fiber catheters such as those manufactured by Mitsubishi Cable of America may be used.

After irrigation of the site so that the stent is surrounded by liquid, energy is delivered to the site. The method of transferring light via fiber optic catheters is well documented in the literature.

The method of Watson U.S. Pat. No. 4,887,600 is one such method in which delivery of laser energy via an optical fiber is employed to generate a shock wave. The method is used to quickly break down a kidney stone to sand like particles. In the case of coronary devices, sand-like particles (greater than 5 micrometers in diameter) would be too large to liberate into the circulatory system. Localized heating must occur within the cardiovascular tissue as opposed to liquid surrounding a kidney stone as described in U.S. Pat. No. 4,887,600.

Certain conditions must be met during the breakdown or degradation process of the present invention. Primarily particles that may be produced should be less than about 1 micrometer in diameter.

Further, gases that are produced should be readily soluble in blood. The use of lactides as the stent material readily meets these criteria, as lactides and glycolides tend to form small crystallites as they degrade and upon oxidation ultimately form carbon dioxide and water. Gases are preferred in that they are the smallest form of particles, i.e. individual molecules. The formation of such gases must be limited both by temperature and by amount so that gaseous emboli do not form.

Limitation of the temperature reached must be limited to prevent blood and tissue damage. The absolute maximum temperature that tissue or blood can be allowed to reach is about 99° C., the temperature at which blood would boil. Substantial denaturation of protein will occur, however, at lower temperatures. A practical maximum temperature time regime is an average temperature of about 60° C. for about one minute.

Such temperature limits can be maintained by using nanosecond to microsecond pulses. In doing so, the ablation process will occur faster than the time required for temperature build up. Excimers which emit light at 308 nm would have to be frequency doubled to avoid ablation of thrombotic material and destruction of blood cells.

In addition, the actual amount of solid material ablated should be limited so that in the event that the material is transformed into a gaseous form, assuming none is absorbed by the blood, would be on the order of a blood cell, i.e. about 200 cubic micrometers. This would require that each pulse ablate about a nanomole of material. With microsecond pulse sequences, a millimole of material could be practically disrupted within a matter of seconds.

So long as the composition of the materials does not itself contain any molecular components that may be construed as carcinogenic or otherwise harmful, the likelihood of the formation of such products upon the application of laser energy is limited.

Energy may be delivered to the site of the stent by means of a catheter with a laser means. A suitable laser would be an excimer laser tuned to a particular wavelength by a selected gas mixture. An excimer laser is a preferred type of laser, as it will produce a breakdown product of approximately 90% vapor. Pulse duration should be in the range of 0.05 to 10 microseconds and power ranges of about 5 to 200 millijoules.

Figure 4:
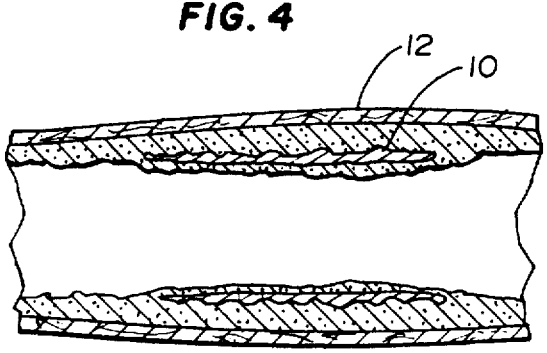
FIG. 4 is a cross sectional view of a vessel in which a biodegradable stent has been in place for a sufficient length of time to be surrounded by tissue.

A shock wave is triggered within the biodegradable stent through application of pulsed laser light via the optical fiber. The optical fiber delivers laser light having an energy per pulse between about 5 millijoules and 200 millijoules and intensity of at least 5 megawatts per square centimeter to the biodegradable stent. It would be preferable to be able to use wavelengths that are not absorbed by blood or by thrombus. The primary chromophore in blood and in thrombi is oxyhemoglobin and this molecule has absorption peaks in the UV due to aromatic contents of proteins and in the visible spectrum at 420, 540 and 570 nm. Lasers emitting ultraviolet light or visible light in these regions would be absorbed by blood, thrombus and tissue. Lasers emitting light between 1000 and 3000 nm would cause heating in blood due to absorption in the infrared region by water. Thus optimum absorption regions for a device, if the system were to avoid absorption by blood, would be in the region between about 600 and 900 nm. Argon and Excimer lasers with frequency doublers are capable of achieving emission in this wavelength region.

Where tissue of vessel 12 surrounds biodegradable polymeric stent 10, such as is shown in FIG. 4, stent 10 may also be pulverized within tissue by sonic blasts of energy accelerating its dissolution and destroying its physical structure. These blasts may be effected internally by means of a laser or externally by delivery of sonic energy. The stent will completely vaporize, thereby obviating the need for removal by physical means.

Figure 5:
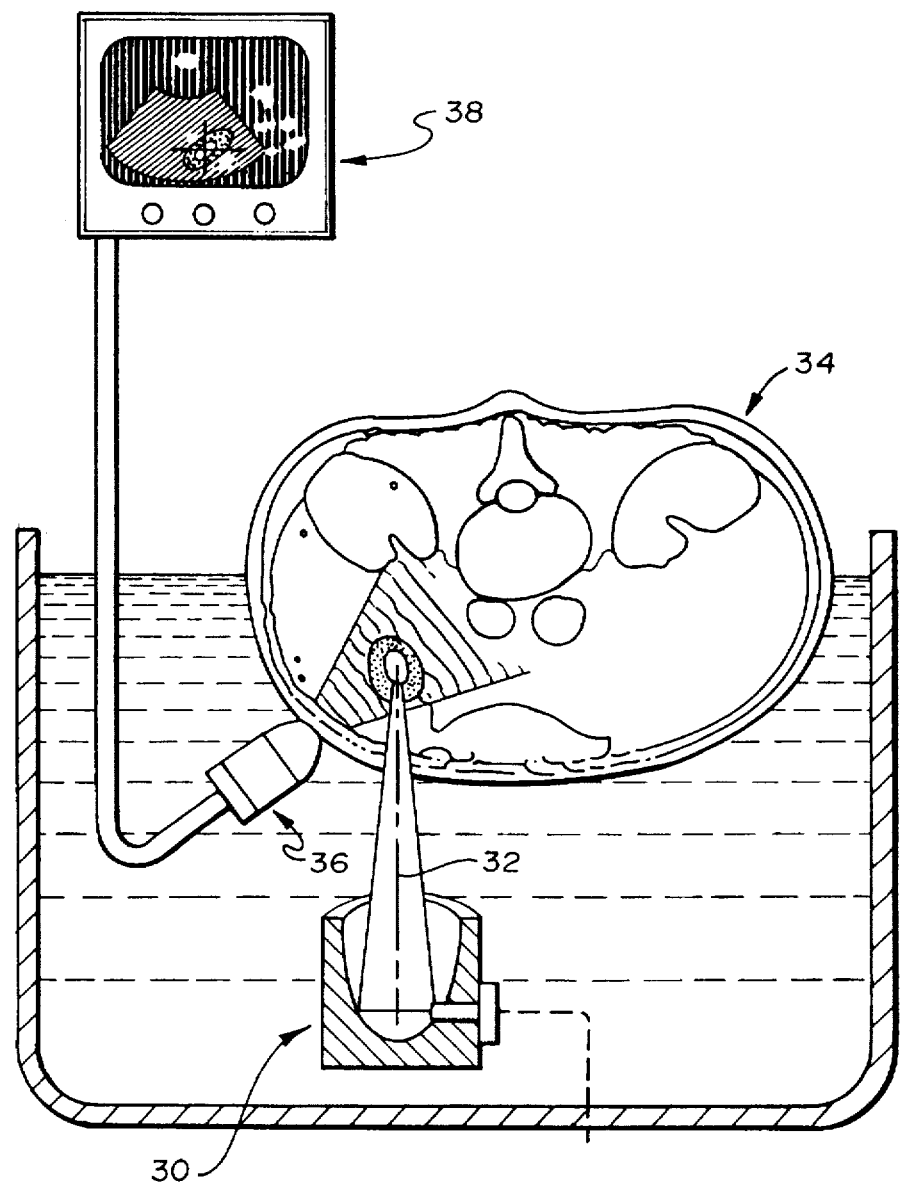
FIG. 5 is a diagrammatic explanation of how ultrasonic waves could be transmitted through the body to a specific location much in the same way as kidney stones are disrupted.

A biodegradable stent may be broken down in an implant site by subjecting the biodegradable stent to at least one blast of energy of sufficient wavelength, intensity, energy per blast and blast duration to break down the stent. The energy blasts may be blasts of sonic energy delivered by extracorporeal means. Referring to FIG. 5, a diagrammatic explanation of how ultrasonic waves could be transmitted through the body to a specific location much in the same way as kidney stones are disrupted is provided.

As shown in the diagram of FIG. 5, extracorporeally generated shock waves may be generated by high-current underwater spark discharge and directed through a water bath into which a patient is immersed.

High energy shock waves are generated by high current underwater spark discharge 30 and directed through water bath 32 into which patient 34 is immersed. The disclosing electrode is placed at one focal point of a semiellipsoidal reflector in order to reflect the shock waves in the second focal point, where stent 10 has been positioned. Shock waves generated in water enter patient 34 and reach stent 10 practically unimpeded if the tissue has an acoustical impedance similar to that of water. Monitoring is preferably effected by ultrasound transducer 36 and monitor 38.

A significant advantage is provided by the present invention through the delivery of sonic bursts of energy through extracorporeal means, although delivery of a laser pulse or sonic energy, either internally, or by means external to the body of the organism in which the stent has been implanted may be utilized.

Another advantage of the present invention is the ability to accelerate the dissolution of a biodegradable polymeric stent by completely destroying the stent by vaporization without a need for any invasive removal procedure. Further, the process is applicable to virtually all biodegradable polymeric stents, as biodegradable polymeric stents tend to become less pliable as degradation proceeds. These devices will become or may be in their original state, sufficiently rigid to be subject to ablation by the method of the present invention. Further, if it is necessary to cure the stent by artificial means, such as through UV radiation, or through heating, or through the reaction of water with materials in the stent devices, this can be effected prior to subjecting the biodegradable polymeric stent to the method of the present invention.

A further advantage of the present invention is its versatility. The method may be used to alter any stent, including those made of metal or polymeric material. The present method also makes it unnecessary to maintain a continuous external connection between a stent and a catheter manifold wire or similar device, thereby preventing continuous exposure of the insertion site to the possibility of infection, and preventing limitation of the mobility of a patient.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method for modifying an implanted stent in an implant site comprising subjecting the stent to blasts of energy of sufficient wavelength, intensity, energy per blast and blast duration to affect the physical structure of the stent without substantially affecting the implant site.

2. The method of claim 1 wherein the stent is made of metal.

3. The method of claim 1 wherein the stent is made of a polymeric material.

4. The method of claim 3 wherein the stent is biodegradable.

5. The method of claim 3 Wherein the stent is made of a material selected from the group consisting of polyethylene terephthalate, PTFE, polylactides, polyglycolides, polycaprolactone, polyesters, polyethylene, carbohydrates, polycarbohydrates, collagen, crosslinked collagen, and combinations thereof.

6. A method of removing an implanted biodegradable stent in an implanted site in an animal body or lumen, the method comprising:

(a) inserting an optical fiber of diameter less than about 600 microns into the body so that the distal end of the fiber can directly illuminate both the biodegradable stent to be destroyed and liquid surrounding the biodegradable stent; and (b) triggering a shockwave within the biodegradable stent through application of pulsed laser light having an energy per pulse between about 5 millijoules and 200 millijoules and intensity of at least 5 megawatts per square centimeter to the biodegradable stent via the optical fiber to cause shockwave fragmentation of the biodegradable stent so that the biodegradable stent is fragmented and none of the surrounding tissue is substantially affected.

7. The method of claim 6 wherein the pulsed laser has a duration of between about 0.05 and 10 microseconds and a wavelength of between about 600–900 nanometers.

8. A method for removing an implanted biodegradable stent from an implant site comprising subjecting the biodegradable stent to an excimer laser pulse of sufficient wavelength, intensity, energy per pulse and pulse duration to vaporize the biodegradable stent without substantially affecting the tissue at the implant site.

9. A method for breaking down an implanted biodegradable stent in an implant site comprising the step of subjecting the biodegradable stent to at least one blast of energy of sufficient wavelength, intensity, energy per blast and blast duration to break down the stent.

10. The method of claim 9 wherein said energy blasts are blasts of sonic energy delivered by extracorporeal means.

11. A method for accelerating the dissolution of an implanted biodegradable stent in an implant site comprising subjecting the biodegradable stent to blasts of energy of sufficient wavelength, intensity, energy per blast and blast duration to vaporize the physical structure of the polymeric stent without substantially affecting the implant site said blasts of energy being provided by an excimer laser.

* * * * *

UNITED STATES PATENT AND TRADEMARK OFFICE
CERTIFICATE OF CORRECTION

PATENT NO. : 5,593,403

DATED : January 14, 1997

INVENTOR(S) : Paul J. Buscemi

It is certified that error appears in the above-identified patent and that said Letters Patent is hereby corrected as shown below:

column 5, line 3, delete "rim" and insert therefor -- nm --, and
column 6, line 62, please insert after the word site -- , --.

Signed and Sealed this

Ninth Day of September, 1997

Attest:

BRUCE LEHMAN

Attesting Officer

Commissioner of Patents and Trademarks